United States Patent
Huang et al.

(10) Patent No.: US 11,918,452 B2
(45) Date of Patent: Mar. 5, 2024

(54) COVERED STENT

(71) Applicant: Lifetech Scientific (Shenzhen) Co., Ltd., Shenzhen (CN)

(72) Inventors: Xinxin Huang, Shenzhen (CN); Caiping Liu, Shenzhen (CN); Benhao Xiao, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 17/778,304

(22) PCT Filed: Nov. 12, 2020

(86) PCT No.: PCT/CN2020/128299
§ 371 (c)(1),
(2) Date: May 19, 2022

(87) PCT Pub. No.: WO2021/098577
PCT Pub. Date: May 27, 2021

(65) Prior Publication Data
US 2023/0000613 A1    Jan. 5, 2023

(30) Foreign Application Priority Data
Nov. 22, 2019  (CN) .......................... 201911156626.0

(51) Int. Cl.
*A61F 2/07* (2013.01)
*A61F 2/89* (2013.01)

(52) U.S. Cl.
CPC . *A61F 2/07* (2013.01); *A61F 2/89* (2013.01)

(58) Field of Classification Search
CPC ...... A61F 2/07; A61F 2220/0016; A61F 2/82; A61F 2002/4415; A61F 2/89;
(Continued)

(56) References Cited

U.S. PATENT DOCUMENTS

2001/0032010 A1* 10/2001 Sandock .................... A61F 2/90
623/1.15
2002/0055775 A1*  5/2002 Carpentier ............ A61F 2/2412
623/2.14
(Continued)

FOREIGN PATENT DOCUMENTS

CN    2427227 Y    4/2001
CN    2605866 Y    3/2004
(Continued)

OTHER PUBLICATIONS

Translation of CN 209392155 (Year: 2019).*
(Continued)

*Primary Examiner* — Brian E Pellegrino
(74) *Attorney, Agent, or Firm* — Raymond Sun

(57) ABSTRACT

A covered stent (100) includes a first wave ring (20) provided on at least one end of the covered stent (100), wherein the first wave ring (20) is formed of braided wires by means of braiding; each of the braided wires has wire heads (21) and a wire rod (22), with the wire heads (21) being located at two ends of the wire rod (22); and the wire heads (21) of the braided wire are wound around the adjacent wire rod (22); and the covered stent (100) further includes a limiting unit (40), with the limiting unit (40) being arranged on the wire head (21) and the wire rod (22) adjacent to the wire head (21), and the limiting unit (40) limiting the range of axial and/or radial movement of the wire head (21) relative to the wire rod (22).

5 Claims, 7 Drawing Sheets

(58) Field of Classification Search
CPC ...... A61F 2210/0076; A61F 2220/0041; A61F 2220/0075; A61F 2/88; A61F 2250/0098; A61F 2250/001; A61F 2/2409; A61F 2250/007; A61B 2017/0461; B21F 15/00; B21F 15/02
USPC .............. 623/1.16, 1.34, 1.22; 606/152, 155
See application file for complete search history.

(56) References Cited

U.S. PATENT DOCUMENTS

| | | | | |
|---|---|---|---|---|
| 2010/0174300 | A1* | 7/2010 | Blondeel | A61B 17/11 606/155 |
| 2011/0040368 | A1 | 2/2011 | Petersen | |
| 2012/0259404 | A1* | 10/2012 | Tieu | A61F 2/88 623/1.15 |
| 2022/0031481 | A1 | 2/2022 | Leng et al. | |

FOREIGN PATENT DOCUMENTS

| | | | | |
|---|---|---|---|---|
| CN | 202508415 U | 10/2012 | | |
| CN | 108095858 A | 6/2018 | | |
| CN | 209107690 U | 7/2019 | | |
| CN | 209392155 U | 9/2019 | | |
| WO | WO-9915109 A2 * | 4/1999 | ............. | A61F 2/82 |
| WO | WO-9932051 A1 * | 7/1999 | ............. | A61F 2/06 |
| WO | WO2018095090 A1 | 5/2018 | | |

OTHER PUBLICATIONS

Office Action dated Mar. 11, 2022 for corresponding India Application No. 202217035273.
Office Action dated Sep. 26, 2021 for corresponding China Application No. 201911156626.0.
Translation of Office Action dated Sep. 26, 2021 for corresponding China Application No. 201911156626.0.
Response to Office Action dated Sep. 26, 2021 for corresponding China Application No. 201911156626.0.
Translation of Response to Office Action dated Sep. 26, 2021 for corresponding China Application No. 201911156626.0.
Amended Claims in Response to Office Action dated Sep. 26, 2021 for corresponding China Application No. 201911156626.0.
Translation of Amended Claims in Response to Office Action dated Sep. 26, 2021 for corresponding China Application No. 201911156626.0.
Notice of Grant dated Mar. 28, 2022 for corresponding China Application No. 201911156626.0.
Translation of Notice of Grant dated Mar. 28, 2022 for corresponding China Application No. 201911156626.0.
International Search Report dated Jan. 28, 2021 for corresponding PCT Application No. PCT/CN2020/128299.
Response to Office Action dated Feb. 11, 2022 for corresponding China Application No. 201911156626.0.
Claims Accompanying Response to Office Action dated Feb. 11, 2022 for corresponding China Application No. 201911156626.0.
Notice of Grant for corresponding China Application No. 201911156626.0.

* cited by examiner

COVERED STENT

FIELD

The present disclosure belongs to the field of medical devices and is specifically relates to a covered stent.

BACKGROUND

In an existing covered stent, a section of the small wave ring with a smaller wire diameter and a smaller wave height than the wave ring of the main body is provided at its ends in order to ensure increased adherence of its ends to a vessel, and increase in sealing performance after implantation of the covered stent, such that the covered stent will not form type I endoleaks due to the gap between an end of the covered stent and a vessel wall after implantation. However, if a stainless steel sheath or a relatively complicated winding method is used to fix the head of the wire, the relatively small diameter of the wire of the small wave ring is likely to cause a breakage or damage of the braided wire, especially of the metal wire, thus resulting in poor fatigue resistance of the covered stent. Therefore, after the completion of the manufacture of the small wave ring, the wire heads are often simply wound around the wire rod, such that the wave ring forms a stable closed ring structure. However, the simply wound wire heads can easily become loose after the stent is compressed and released, and the loose wire heads can easily tilt upwards, which can cause breakage of the covering film and destroy the stability of the covering film, such that type IV endoleak is easily produced due to the excessive pore size after implantation of the covered stent. In addition, the tilting wire heads can easily catch the covering film on the opposite side, making the deployment of the bare stent incomplete after the implantation of the covered stent (as shown in FIG. 1), resulting in type I endoleak after implantation, and even resulting in displacement of the covered stent under the impact of blood flow, thereby affecting the therapeutic effect of the device, which may even require the doctor to perform other means of intervention during the surgery, causing an increase in surgical risk and the cost burden for patients.

SUMMARY

In view of problems above, it is an objective of the present disclosure to solve at least the problem of easily loosened wire heads of the first wave ring in the prior art. The objective is achieved through the following technical solution:

Embodiments of the present disclosure provide a covered stent including a first wave ring provided on at least one end of the covered stent, wherein the first wave ring is formed of braided wires by means of braiding, each of the braided wires has wire heads and a wire rod, with the wire heads being located at two ends of the wire rod; and the wire heads of the braided wire are wound around the adjacent wire rod; and the covered stent further includes limiting units, with each of the limiting units being arranged on the wire head and the wire rod adjacent to the wire head, and the limiting unit limiting the range of axial and/or radial movement of the wire head relative to the wire rod.

In some embodiments of the present disclosure, the limiting unit includes a strip structure provided on the wire head and the wire rod adjacent to the wire head in a spirally wound manner.

In some embodiments of the present disclosure, the strip structure is made of hot-melt material and is bonded to the wire rod and the wire head by means of heat treatment.

In some embodiments of the present disclosure, a plurality of spiral sections is formed after the strip structure is spirally wound around the wire head and the wire rod, wherein at least one spiral section covers an end of the wire head, and the spacing between two spiral sections closest to the end of the wire head is less than the diameter of the wire rod.

In some embodiments of the present disclosure, the limiting unit includes at least two first projections provided on the wire head and at least one second projection provided on the wire rod adjacent to the wire head, with the second projection being located between the two adjacent first projections; or the limiting unit includes at least one first projection provided on the wire head and at least two second projections provided on the wire rod adjacent to the wire head, with the first projection being located between the two adjacent second projections.

In some embodiments of the present disclosure, the spacing between the two adjacent first projections is greater than or equal to the length of the second projection and less than or equal to 1.5 times the length of the second projection; and/or the spacing between the two adjacent second projections is greater than or equal to the length of the first projection and less than or equal to 1.5 times the length of the first projection.

In some embodiments of the present disclosure, the limiting unit includes a structure formed by successively winding a strip material on the wire head and the wire rod in a staggered manner.

In some embodiments of the present disclosure, a contact surface between the braided wire and the limiting unit is provided with bumps or dimples, or the contact surface is roughened.

In some embodiments of the present disclosure, the covered stent further includes a covering unit covering at least an end of the wire head.

The advantages of the present disclosure are that:

The present disclosure provides a covered stent, of which a first wave ring is formed of braided wires by means of braiding, and heads of a braided wire are wound around an adjacent wire rod, and the covered stent also has a limiting unit, which limits the range of axial and/or radial movement of the wire head relative to the wire rod along the wire head. Since the axial movement of the wire heads relative to the wire rods along the wire heads is limited, the wire heads which are wound around the wire rods are not prone to becoming loose, which can enhance the structural stability of the first wave ring and is also conducive to preventing the wire heads from tilting upwardly, thereby protecting the covering film to a certain extent.

BRIEF DESCRIPTION OF THE DRAWINGS

The drawings are only for purposes of illustrating the preferred implementations and are not to be construed as limiting the present disclosure. Also, throughout the drawings, the same reference numerals represent the same components. In the drawings.

DETAILED DESCRIPTION OF THE DISCLOSURE

Figure 1:
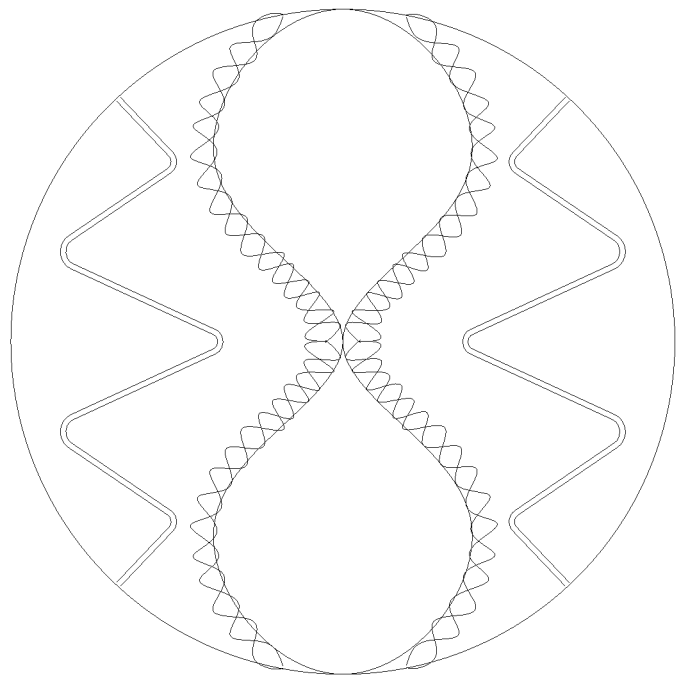
FIG. 1 is a schematic view of a covered stent under incomplete deployment in the prior art.

Exemplary implementations of the present disclosure will be described in more detail below with reference to the accompanying drawings. Although the drawings show the exemplary implementations of the present disclosure, it should be understood that the present disclosure may be implemented in various forms and should not be limited to the implementations described herein. Instead, these implementations are provided such that the present disclosure can be understood more thoroughly, and can fully convey the scope of the present disclosure to those skilled in the art.

It should be understood that the terms used herein are for the purpose of describing specific example implementations only, and are not intended to give any limitation. As used herein, the singular forms "a/an", "one" and "the" may also include plural forms, unless the context clearly indicates otherwise. The terms "comprise", "include", "contain" and "have" are inclusive, and indicate the existence of features, steps, operations, elements and/or components stated, but do not exclude the existence or addition of one or more other features, steps, operations, elements, components, and/or combinations thereof. The method steps, processes, and operations described herein are not to be construed as necessarily requiring them to be executed in the particular order described or illustrated, unless the order of execution is explicitly indicated. It should also be understood that additional or alternative steps may be used.

Although the terms first, second, third, etc. may be used herein to describe a plurality of elements, components, regions, layers and/or sections, these elements, components, regions, layers and/or sections should not be limited by these terms. These terms may be used solely to distinguish one element, component, region, layer or section from another region, layer or section. The terms such as "first", "second", and other numerical terms are not used to imply an order or sequence herein unless it is clearly indicated in the context. Thus, a first element, component, region, layer or section discussed below could be termed a second element, component, region, layer or section without departing from the teachings of the example implementations.

To facilitate description, spatially relative terms, such as "inside", "outside", "medial", "lateral", "under", "below", "over", "above", may be used herein to describe the relationship of an element or feature relative to another element or feature as illustrated. Such spatially relative terms are intended to encompass different orientations of the device in use or in operation in addition to the orientations depicted in the drawings. For example, if a device in a drawing is turned over, elements described as "under other elements or features" or "below other elements or features" would then be oriented as "over other elements or features" or "above other elements or features". Thus, the example term "below" can encompass both an orientation of above and below. The device may be oriented otherwise (rotated by 90 degrees or in other directions) and will be interpreted by the spatially relative descriptors used herein accordingly.

In the field of interventional medical devices, especially for implants (such as stents) implanted in the body, the direction of blood inflow is defined as "proximal end" and the direction of blood outflow as "distal end", and the "proximal end" and "distal end" of any component of the medical device are defined according to this principle.

Embodiment 1

Figure 2:
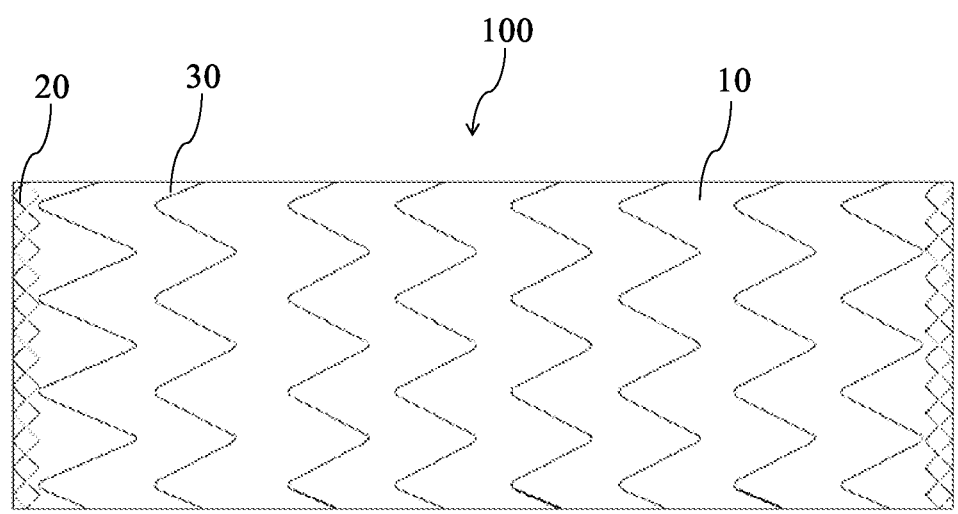
FIG. 2 is a structural schematic view of a covered stent according to an embodiment of the present disclosure.

As shown in FIG. 2, one of the embodiments of the present disclosure provides a covered stent 100 including a plurality of W-shaped wave rings and a covering film 10 through which the plurality of wave rings is connected. Specifically, the wave rings include a first wave ring 20 provided on at least one end of the covered stent 100 and a second wave ring 30 arranged at intervals along the length of the covered stent 100, and the first wave ring 20 is the one closest to the end of the covering film connected to the covering film 10 on the covered stent 100; i.e., if the first wave ring is provided on the proximal end of the covered stent, no other wave rings will be provided on the proximal end of the first wave ring. The first wave ring 20 of the embodiment includes a double-layer W-shaped wave ring, and the "amplitude" of the first wave ring 20 is less than that of the second wave ring 30, and the wire diameter of the braided wires of the first wave ring 20 is also less than that of the second wave ring 30. Further, the covering film 10 may be a material having good biocompatibility, such as PET (Polyethylene terephthalate) material, PTFE (Polytetrafluoroethylene) material, etc.

It should be understood that, in the present disclosure, the second wave ring is larger than the first wave ring in both wire diameter and amplitude, such that the first wave ring is softer than the second wave ring, and the first wave ring is provided on the end of the covered stent mainly in order to improve the adherence performance of the end of the covered stent, and to prevent the occurrence of endoleak.

It will be appreciated that in other embodiments, the first wave ring may be provided with one ring or may be provided with multiple rings (i.e., a plurality of first wave rings that are axially arranged); similarly, the first wave ring may be provided with a multi-layer W-shaped wave ring.

Figure 3:
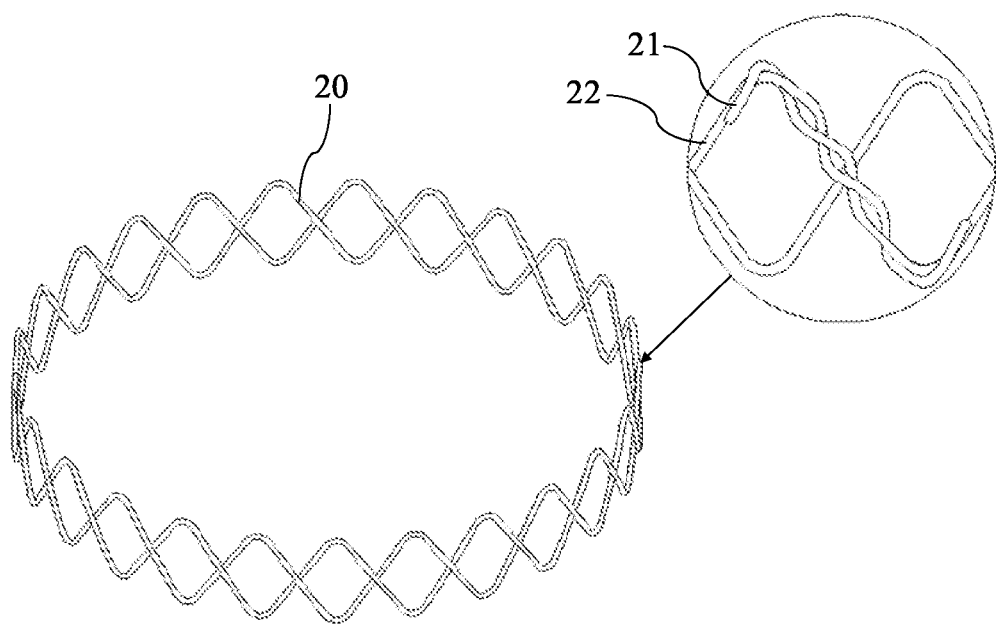
FIG. 3 is a schematic view of a first wave ring and wire head structure of a covered stent of an embodiment of the present disclosure (the limiting unit is not shown)

Referring to FIG. 3, the first wave ring 20 of this embodiment is formed by braiding a single braided wire including wire heads 21 and a wire rod 22, and the wire heads 21 of the braided wire are wound around the wire rod 22 adjacent to the wire heads 21. It will be appreciated that in other embodiments, the first wave ring may be formed by interweaving two braided wires, in which case the ends of the braided wires may be wound around the wire rods in the same manner as in this embodiment.

Figure 4:
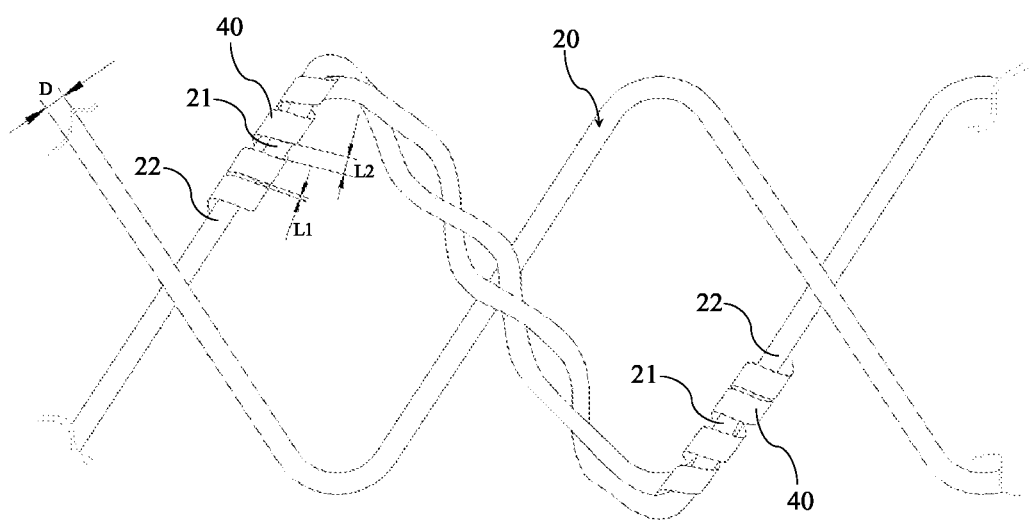
FIG. 4 is a structural schematic view of a first wave ring of a covered stent of an embodiment of the present disclosure.

As shown in FIG. 4, the covered stent 100 further includes a limiting unit 40, and each of the limiting unit 40 is provided on the wire head 21 of the braided wire and the wire rod 22 adjacent to the wire head, and the limiting unit 40 limits the range of axial and radial movement of the wire head 21 relative to the wire rod 22. Since the movement of the wire heads 21 relative to the wire rods 22 along the wire heads is limited, the wire heads 21 wound around the wire rods 22 are not prone to becoming loose, which can enhance the structural stability of the first wave ring and is also conducive to preventing the wire heads 21 from tilting upwardly, thereby protecting the covering film 10 to a certain extent.

Further, each of the limiting unit 40 may be a strip structure, which fixes the wire head 21 with the wire rod 22 in a spirally wound manner, and under the spiral winding of the strip component, the wire head 21 and the wire rod 22 are in close contact and exert pressure on each other, so that when the wire head 21 experiences a movement relative to the wire rod 22, the wire head 21 will be simultaneously subjected to a double friction of both the limiting unit 40 and the wire rod 22, such that its axial and radial movement cannot easily occur, thereby preventing the wire head 21 from becoming loose.

And further, the strip component may be made of hot-melt material having a good biocompatibility, such as PTFE, and the strip structure made of the hot-melt material is bonded to the wire rod 22 and the wire head 21 by means of heat treatment, thereby further reinforcing the wire head 21 and the wire rod 22 to ensure that the wire head 21 does not move axially and radially relative to the wire rod 22, which further eliminates the possibility of the wire head 21 becoming loose.

Still further, the limiting unit 40 is spirally wound around the wire head 21 and the wire rod 22 to form a plurality of spiral sections, wherein one spiral section covers an end of the wire head 21, thereby preventing the end of the wire head 21 from moving in a direction away from the wire rod 22, which may result in the end tilting upwardly; thus, the limiting unit prevents the wire head from breaking the covering film 10. In addition, in the process of spirally winding the strip structure, the winding is denser at a position closer to the end of the wire head 21; i.e., the spacing between the spiral sections becomes smaller. In order to further ensure that the end of the wire head 21 will not be exposed from the gap between the spiral sections, the spacing L1 between the first spiral section and the second spiral section can be made less than the spacing L2 between the second spiral section and the third spiral section, and L2 can be made less than the diameter D of the wire rod 22 (i.e., the wire diameter of the braided wire), such that exposure of the end of the wire head 21 can be strictly avoided.

Embodiment 2

Figure 5:
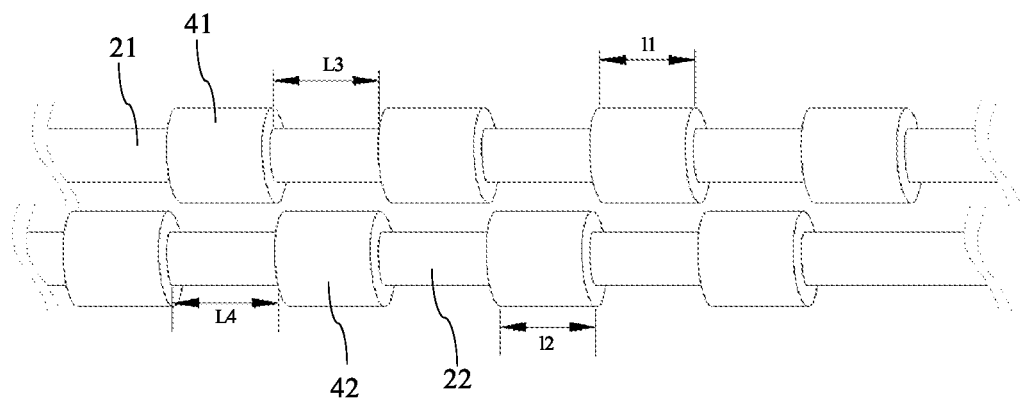
FIG. 5 is a structural schematic view of a first wave ring of a covered stent of an embodiment of the present disclosure when wire heads are not wound around wire rods.
Figure 6:
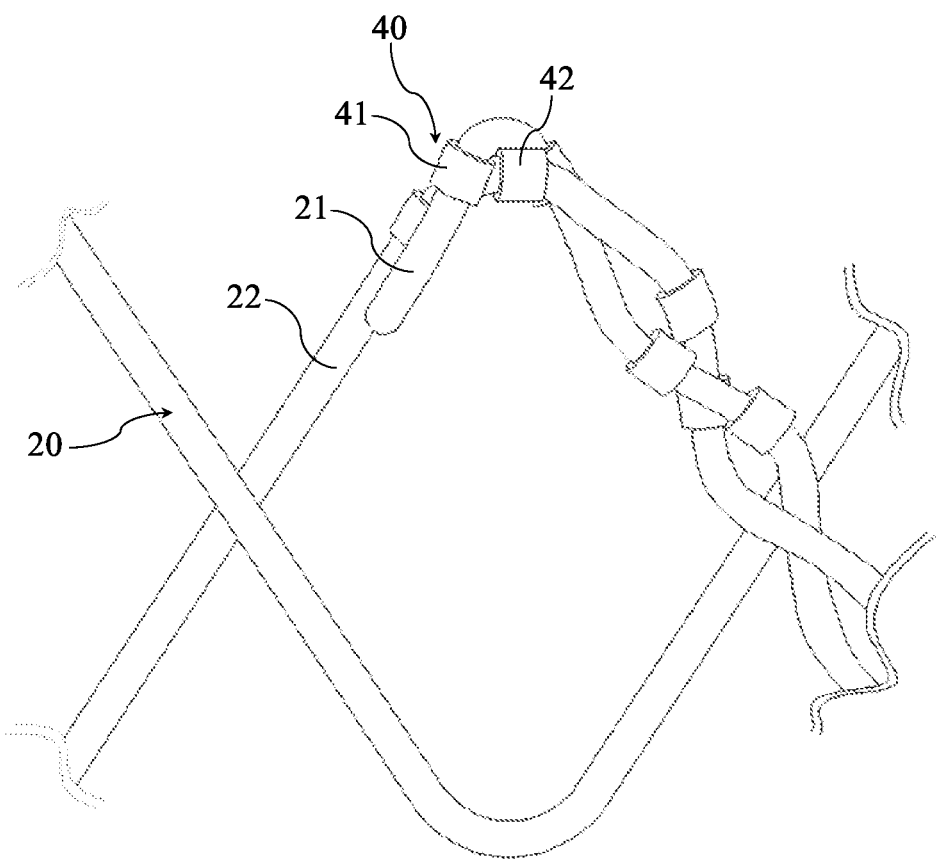
FIG. 6 is a structural schematic view of a first wave ring of a covered stent of an embodiment of the present disclosure.

As shown in FIG. 5 and FIG. 6, another embodiment of the present disclosure provides a covered stent, which is substantially the same as the one in the first embodiment except for the structure of the limiting unit 40.

FIG. 5 shows the structure of a first wave ring of the embodiment when wire heads are not wound, and specifically, the limiting unit 40 includes a plurality of first projections 41 provided on the wire head 21 at intervals and a plurality of second projections 42 provided on the wire rod 22 at intervals. The first projections 41 and the second projections 42 are staggered along the longitudinal direction of the braided wire such that the first projections 41 and the second projections 42 can abut against each other when the wire head 21 has a tendency to move axially along the wire head relative to the wire rod 22, thereby increasing the frictional force between the wire head 21 and the wire rod 22, thus avoiding the wire head 21 moving axially, and further preventing the loosening of the wire head 21; the relative positions of the first projections 41 and the second projections 42 after winding the wire head and the wire rod can be seen in FIG. 6.

It will be appreciated that the present disclosure is not limited to a specific number of the first projections and the second projections, but it should meet the requirement that both ends of at least one of the first projections can be blocked by the second projections. Or both ends of at least one of the second projections can be blocked by the first projections. In other words, the limiting unit includes at least two first projections fixed on the wire head at intervals and at least one second projection fixed on the wire rod adjacent to the wire head, wherein the at least one second projection is located between the two first projections; or the limiting unit includes at least one first projection fixed on the wire head at intervals and at least two second projections fixed on the wire rod adjacent to the wire head, wherein the at least one first projection is located between the two second projections.

It should be understood that the limiting unit 40 of the embodiment is provided only on the portion of the braided wire close to the wire head and on the wire rod adjacent to the portion, and need not be provided for all the wire portions where the wire head and the wire rod are wound.

Further, the limiting unit 40 of the embodiment may have a cylindrical structure, and end surfaces of the cylindrical structure may be relatively easily abutted against each other, thereby serving to increase frictional force between the wire head 21 and the wire rod 22.

Further, the spacing L3 between two adjacent first projections 41 is greater than or equal to the length 12 of the second projection 42 which refers to the dimension of the second projection 42 in axial direction of the wire rod, and less than or equal to 1.5 times the length 12 of the second projection 42. If the spacing between the first projections 41 is too small, the first projections 41 and the second projections 42 can only partially abut against or cannot abut against each other, which may prevent the friction between the wire head 21 and the wire rod 22 from being increased; instead, if the spacing between the first projections 41 is too large, when the first wave ring 20 is subjected to a force, the first projections 41 will move axially along with the wire head 21 by a certain distance, so as to abut against the second projections 42, thereby increasing the frictional force between the wire head 21 and the wire rod 22, but at this time, the wire head 21 may have already damaged the covering film 10 or the covered stent 100.

Similarly, the spacing L4 between two adjacent second projections 42 is greater than or equal to the length 11 of the first projection 41 which refers to the dimension of the first projection 41 in axial direction of the wire head, and less than or equal to 1.5 times the length 11 of the first projection 41.

Further, the limiting units 40 of the embodiment are formed by winding a soft material (e.g. PTFE) on the braiding. Since the surface friction of the soft material is relatively high, it is advantageous to increase the frictional force between the wire heads 21 and the wire rods 22. In addition, it is also advantageous to reduce wear between the first projections 41 and the second projections 42. Specifically, the soft material will play a buffering role when the first projections 41 and the second projections 42 are brought into contact with each other, and therefore it is possible to prevent wear-out failure due to the material being excessively hard, and it can also improve the service life of the first projections 41 and the second projections 42. It will be appreciated that in other embodiments the limiting units may be made of other materials having a lower stiffness than the braided wires, such as PET. And further, the soft material may be fixed to the braided wires by heat treatment.

Figure 7:
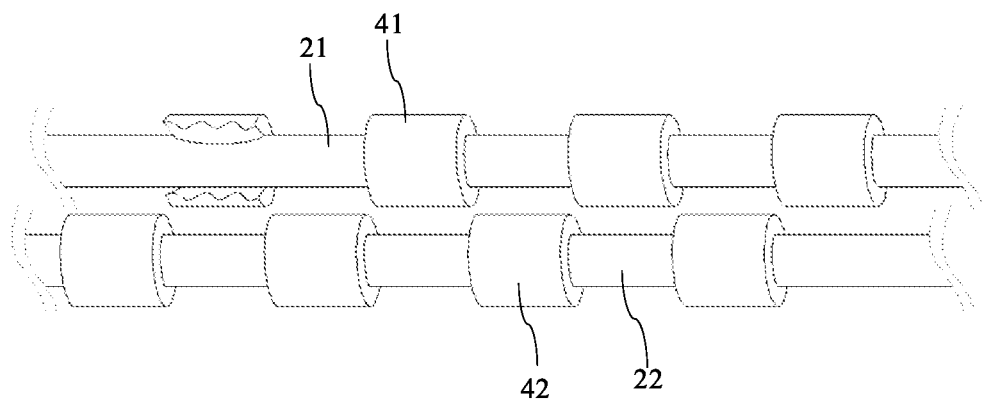
FIG. 7 is a schematic view of a first wave ring of an embodiment of the present disclosure when the surface of the first wave ring is provided with bumps or dimples.

Still further, as shown in FIG. 7, bumps or dimples are formed on the contact surfaces of the braided wires and the limiting unit 40 to increase frictional force. Specifically, especially when the first wave ring 20 is made of metal wires, it is difficult to fix the first projections 41 when they are disposed on the surface of the metal wires, and the frictional force and the connecting force between the metal wires and the first projections 41 are small, such that the first projections 41 are easily displaced from the wire heads 21, thereby causing the limiting function to fail. For this reason, bumps or dimples are provided on the contact surfaces of the wire heads 21 and the first projections 41, thereby increasing the contact area between the metal wires and the first projections 41, and increasing the frictional force and the connecting force therebetween, to prevent the first projections 41 from being displaced relative to the wire heads 21. Similarly, the contact surfaces of the wire rods 22 and the second projections 42 are also provided with bumps or dimples for increasing the frictional force, thereby increasing the contact area between the wire rods 22 and the second projections 42, and increasing the frictional force and connecting force therebetween, to prevent the second projections 42 from being displaced relative to the wire rods 22.

Figure 8:
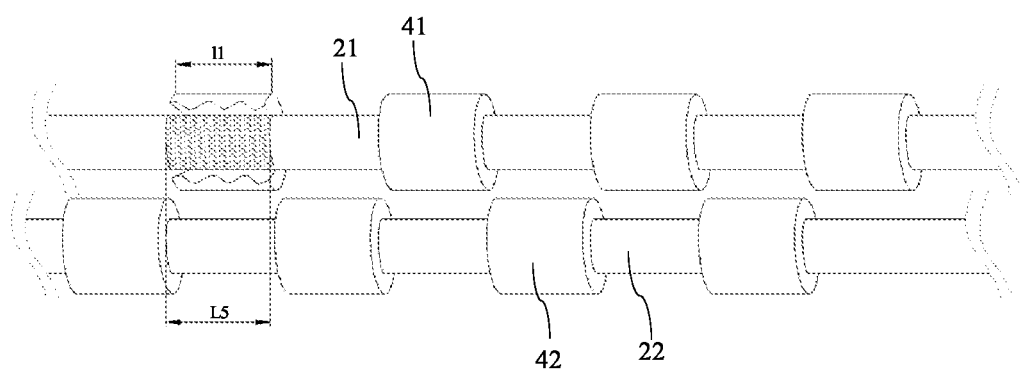
FIG. 8 is a structural schematic view of a first wave ring of an embodiment of the present disclosure when the surface of the first wave ring is provided with a roughening treatment.

In other implementations, as shown in FIG. 8, roughening may also be applied to the surfaces of the braided wires to increase the friction between the braided wires and the first projections 41 and/or the second projections 42. Specifically, the length L5 of a surface-treated portion of the braided wire should be less than the length of the corresponding first projections 41 or the length 12 of the corresponding second projections 42. If the length of the surface-treated portion of the braided wire is too small, the frictional force and the connecting force are not increased, and if the length of the surface-treated portion is too large, a portion of the treated braided wire will be easily exposed, thereby resulting in a decrease in strength and corrosion resistance of the exposed portion, and further reducing the service life of the first wave ring 20.

Further, as shown in FIG. 9-FIG. 12, in other embodiments, the covered stent further includes a covering unit 50 covering at least an end of the wire head 21. Since the covering unit 50 covers the end of the wire head 21, even if the wire head 21 moves to some extent in the axial or radial direction of the wire head, the end of the wire head 21 can be prevented from breaking the covering film and from catching the covering film, thereby protecting the covering film and the covered stent.

Figure 9:
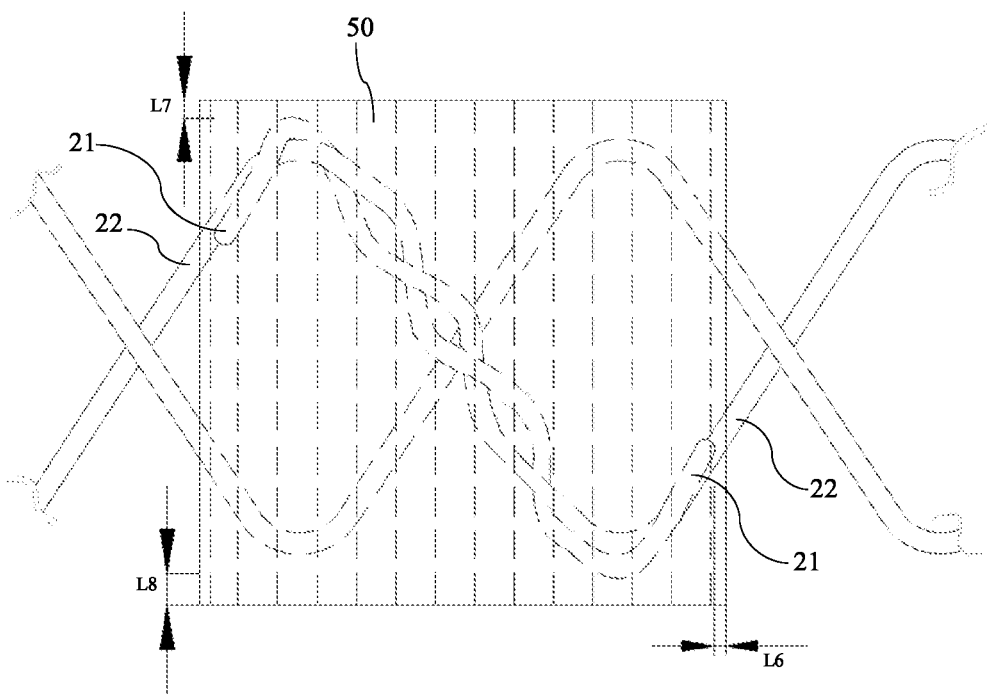
FIG. 9 is a schematic view of a first wave ring of a covered stent of an embodiment of the present disclosure when the first wave ring is provided with a covering unit (covering an area where wire heads and wire rods are wound)

In some specific implementations, as shown in FIG. 9, the covering unit 50 completely covers the area where wire heads 21 and wire rods 22 are wound, thereby limiting the range of movement of the wire heads 21 in the radial direction of the wire rods. The covering unit 50 may be made of a material having pores smaller than the wire diameter of the braided wire as well as good biocompatibility and fracture-resistance, so as to prevent the ends of the wire heads 21 from penetrating out of the gaps of the covering unit 50 or bursting the covering unit 50, which may damage the covering film 10. In addition, the spacing L6 between the edge of the covering unit 50 and the wire heads 21 and the spacing L7 between the edge of the covering unit 50 and the wave crest and wave trough of the first wave ring 20 need to be greater than 0.5 times the wire diameter of the braided wire, such that the covering unit 50 can cooperate with the fixing structure 40 to provide a certain axial movement space for the wire heads 21, and prevent the wire heads 21 of the first wave ring 20 from being tightly bound, which may, after the covered stent 100 is assembled and compressed, cause stress concentration of the first wave ring 20, and then produce micro-cracks affecting the fatigue resistance performance of the first wave ring 20.

The covering unit 50 of the embodiment may be fixed on the first wave ring 20 by heat treatment or may be fixed on the covering film by suture. When suture is adopted, the suture area of the covering unit 50 is shown in FIG. 9. The running direction of the suture needle shall be parallel to the axis of the covered stent, and the suture spacing (the distance between two suture points between visible suture lines outside of the covered stent) L8 shall be less than the wire diameter of the braided wire, so as to avoid other components of the covered stent from hanging on the suture line of the covering unit 50.

Figure 10:
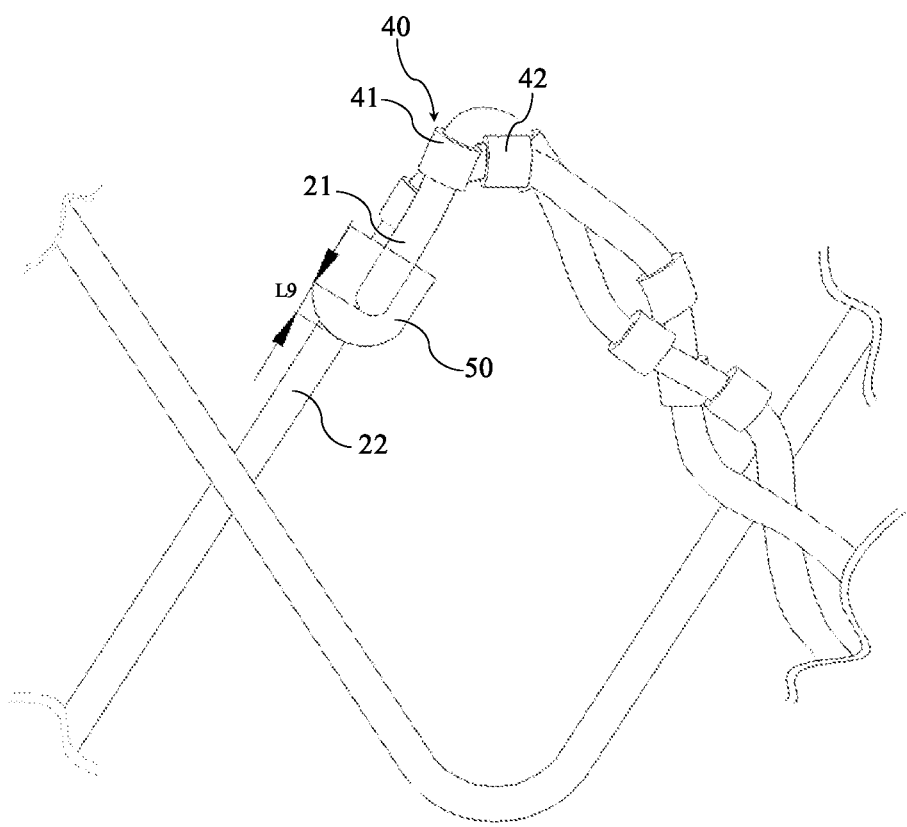
FIG. 10 is a schematic view of a first wave ring of a covered stent of an embodiment of the present disclosure when the first wave ring is provided with a covering unit (covering only an end of a wire head)

In other specific implementations, as shown in FIG. 10, the covering unit 50 covers only the end of the wire head 21. Since the covered stent is assembled into a delivery sheath before it is delivered to the lesion site of the patient, in order to prevent the covering unit 50 from affecting the diameter of the delivery sheath required for the assembly of the covered stent (making the diameter of the delivery sheath larger), the covering unit 50 is disposed only at the end of the wire head 21. Specifically, it is also possible to make the distance L9 between the edge of the covering unit 50 and the wire head 21 greater than or equal to 0.5 times the wire diameter of the braided wire, thereby ensuring that the covering unit 50 completely covers the end of the wire head 21 and providing a certain movement space for the wire head 21 to prevent the stress concentration of the first wave ring 20 after the covered stent is assembled and compressed due to over-tightening, which may result in a decrease in the fatigue resistance strength of the first wave ring 20.

Figure 11:
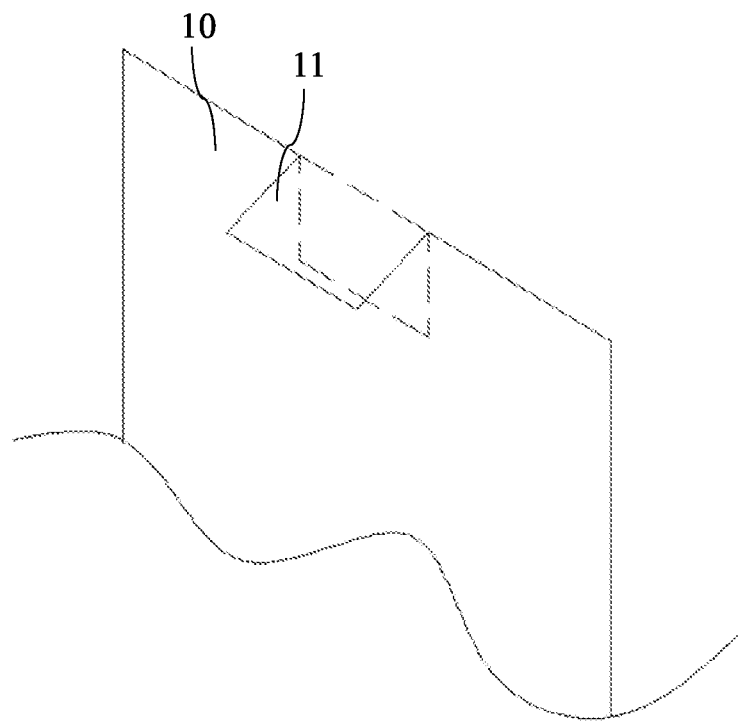
FIG. 11 is a schematic diagram of the formation of a covering unit of a covered stent of an embodiment of the present disclosure.
Figure 12:
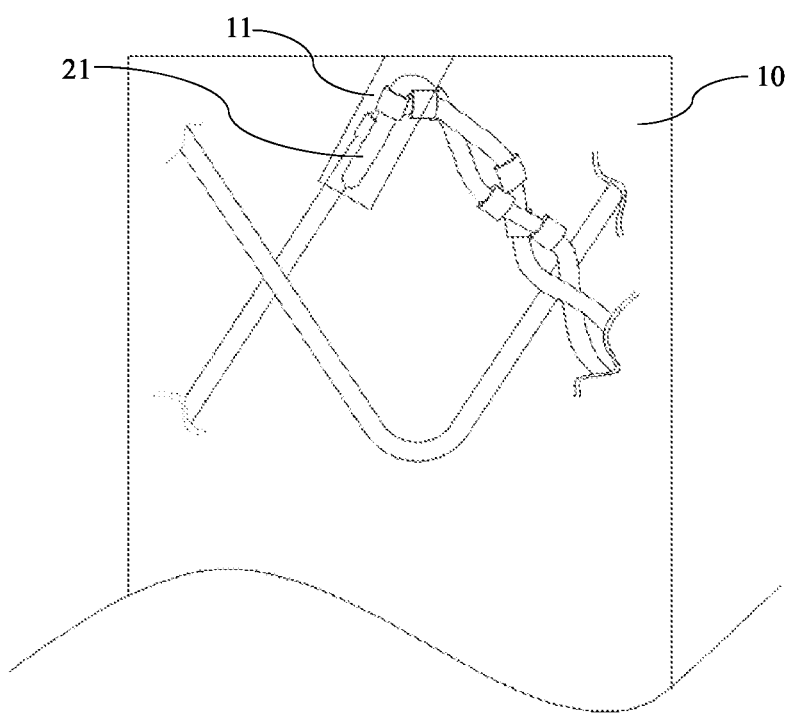
FIG. 12 is a schematic diagram showing the effect of a covering unit of a covered stent of an embodiment of the present disclosure.

In addition, the covering unit 50 may also be a part of the covering film, and specifically, as shown in FIG. 11, a protrusion segment 11 may be integrally provided on the covering film 10. When the first wave ring 20 is fixed on the covering film 10, the wire head 21 of the first wave ring 20 has to be placed in the area covered by the protrusion segment 11, and then the protrusion segment 11 is folded to ensure that the protrusion segment 11 can completely cover the wire end 21 or the area where the wire end 21 and the wire rod 22 are wound. Specifically, as shown in FIG. 12, the protrusion segment 11 for covering the wire head 21 may be cut independently during the process of manufacturing the covering film 10, and since the protrusion segment 11 has one side connected with the covering film 10, there are relatively fewer sides required to be fastened later, thereby reducing the difficulty and time of disposing the covering unit 50.

Embodiment 3

Figure 13:
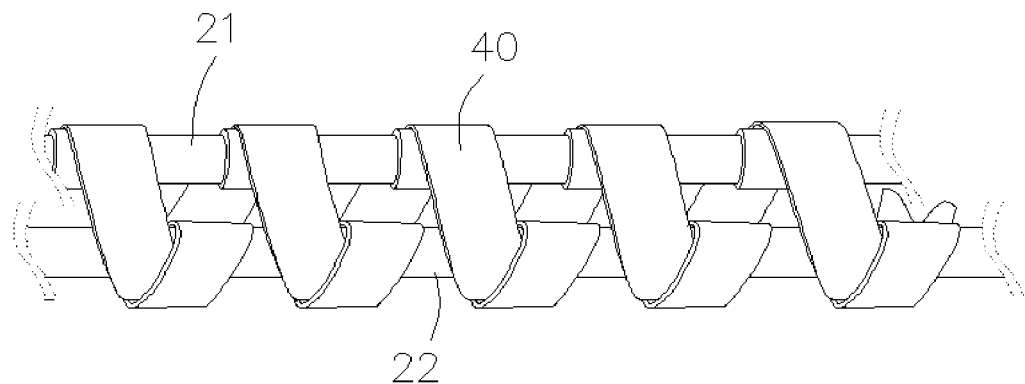
FIG. 13 is a schematic view of a first wave ring of a covered stent of an embodiment of the present disclosure.

As shown in FIG. 13, another embodiment of the present disclosure provides a covered stent, which is substantially the same as the one in the second embodiment except for the structure of the limiting unit 40.

Specifically, the limiting unit 40 is a structure formed by successively winding a strip material on the wire head 21 and the wire rod 22 in a staggered manner, and the structure is formed by winding the strip material from the beginning to the end, thereby saving time for disposing the limiting unit 40 and improving disposal efficiency. Also, since the limiting unit 40 is formed by winding a strip material on the wire head 21 and the wire rod 22 successively in a staggered manner, the limiting unit 40 connects the wire head 21 and the wire rod 22 together, thereby limiting the distance between the wire head 21 and the wire rod 22, thus limiting the range of radial movement of the wire head 21, facilitating disposal of the smaller limiting unit 40, and therefore reducing the diameter of the covered stent 100 assembled into the sheath. In addition, when the wire head 21 of the first wave ring 20 moves, a certain backward pulling force is provided which may prevent the wire head 21 from moving further.

Figure 14:
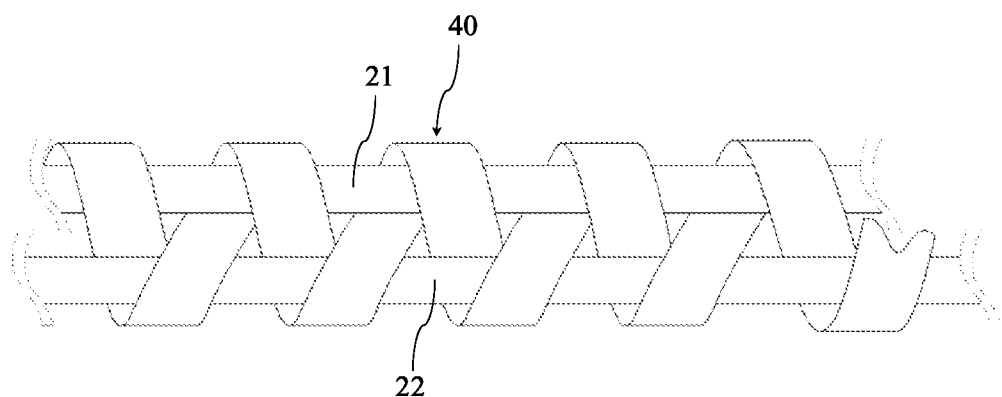
FIG. 14 is a schematic view of a first wave ring of a covered stent of an embodiment of the present disclosure.

It will be appreciated that the limiting unit 40 may be formed in the manner shown in FIG. 13, i.e., by winding a strip material around the wire rod for one turn and then onto the same side of the wire head, winding around the wire head for one turn and then onto the same side of the wire rod, and so on, thus forming a staggered wound structure. The limiting unit 40 can also be formed in the manner shown in FIG. 14, i.e., the strip material passes through the middle between the wire head and the wire rod, winds to the other side of the wire rod, wraps around the wire rod, and passes through the other side of the wire rod, passes through the middle between the wire head and the wire rod again to the other side of the wire head, and wraps around the wire head, and so on, thus forming a staggered wound structure.

The above descriptions are merely better specific implementations of the present disclosure, but the protection scope of the present disclosure is not limited thereto. Any skilled person who is familiar with this art could readily think of variations or substitutions within the disclosed technical scope of the present disclosure, and these variations or substitutions shall fall within the protection scope of the present disclosure. Therefore, the protection scope of the present disclosure shall be subjected to the protection scope of the claims.

The invention claimed is:

1. A covered stent, comprising a covering film and a first wave ring provided on at least one end of the covered stent, wherein the first wave ring does not exceed the covering film, the first wave ring is formed of braided wires by means of braiding, each of the braided wires has wire heads and a wire rod, with the wire heads being located at two ends of the wire rod, and the wire heads of the braided wire are wound around the adjacent wire rod, wherein that the covered stent further comprises a limiting unit, with the limiting unit being arranged on the wire head and the wire rod adjacent to the wire head, and the limiting unit limiting the range of axial and/or radial movement of the wire head relative to the wire rod; and the limiting unit comprises at least two first projections provided only on the wire head and at least one second projection provided only on the wire rod adjacent to the wire head, the second projection being located between the two adjacent first projections; or the limiting unit comprises at least one first projection provided only on the wire head and at least two second projections provided only on the wire rod adjacent to the wire head, the first projection being located between the two adjacent second projections.

2. The covered stent of claim 1, wherein a spacing between the two adjacent first projections is greater than or equal to the length of the second projection and less than or equal to 1.5 times the length of the second projection;

and/or a spacing between the two adjacent second projections is greater than or equal to the length of the first projection and less than or equal to 1.5 times the length of the first projection.

3. The covered stent of claim 1, wherein a contact surface between the braided wire and the limiting unit is provided with bumps or dimples, or the contact surface is roughened.

4. The covered stent of claim 3, wherein the covered stent further comprises a covering unit covering at least the end of the wire head.

5. The covered stent of claim 1, wherein that the covered stent further comprises a covering unit covering at least the end of the wire head.

* * * * *